US007510546B2

(12) United States Patent
Baessler et al.

(10) Patent No.: US 7,510,546 B2
(45) Date of Patent: Mar. 31, 2009

(54) HEAD PART FOR A MULTI-CHAMBER TUBE BAG

(75) Inventors: Armin Baessler, Koenigsbrunn (DE); Herbert Ginter, Kaufbeuren (DE); Ralf Willner, Tussenhausen (DE)

(73) Assignee: Hilti Aktiengesellschaft, Schaan (LI)

( * ) Notice: Subject to any disclaimer, the term of this patent is extended or adjusted under 35 U.S.C. 154(b) by 464 days.

(21) Appl. No.: 10/964,322

(22) Filed: Oct. 13, 2004

(65) Prior Publication Data

US 2005/0085786 A1 Apr. 21, 2005

(30) Foreign Application Priority Data

Oct. 15, 2003 (DE) ................................ 103 47 938

(51) Int. Cl.
*A61B 19/00* (2006.01)

(52) U.S. Cl. ....................... 604/408; 604/403; 222/139; 222/145.1; 222/485; 222/488

(58) Field of Classification Search ................. 604/408, 604/403; 222/139, 145.1, 485, 488
See application file for complete search history.

(56) References Cited

U.S. PATENT DOCUMENTS

| | | | | |
|---|---|---|---|---|
| 3,323,682 | A | 6/1967 | Creighton et al. | |
| 4,340,154 | A * | 7/1982 | VanManen | 222/94 |
| 4,366,919 | A * | 1/1983 | Anderson | 222/137 |
| 5,647,510 | A * | 7/1997 | Keller | 222/94 |
| 5,897,028 | A * | 4/1999 | Sauer | 222/82 |
| 6,634,524 | B1 * | 10/2003 | Helmenstein | 222/94 |

* cited by examiner

*Primary Examiner*—Tatyana Zalukaeva
*Assistant Examiner*—Ginger T Chapman
(74) *Attorney, Agent, or Firm*—Abelman, Frayne & Schwab

(57) ABSTRACT

A head part (11) for a multi-chamber tube bag (1) with a multi-component mass which can be pressed out, having a main chamber (2) for a first component and two secondary chambers (3, 4) for two other components, has a disk-shaped contact surface (12) for the multi-chamber tube bag (1) surrounding a press-out opening (13). At the contact surface (12), a plurality of raised portions (14) project toward the multi-chamber tube bag (1) and are provided at the head part (11) for narrowing the outlet regions (5, 6) of the two secondary chambers (3, 4) of the multi-chamber tube bag (1) when the multi-chamber tube bag (1) bears against the contact surface (12).

2 Claims, 3 Drawing Sheets

HEAD PART FOR A MULTI-CHAMBER TUBE BAG

FIELD OF THE INVENTION

The invention is directed to a head part for a multi-chamber tube bag with a multi-component mass which can be pressed out, having a main chamber for a first component and at least one secondary chamber for another component. The head part has a substantially flat contact surface for the multi-chamber tube bag surrounding a press-out opening.

DESCRIPTION OF THE PRIOR ART

Multi-component chemical masses are used in different areas of day-to-day life and particularly in construction, e.g., as mortar, glue, sealing compound or insulating foam. The masses mostly comprise a hardener, a component to be hardened, and fillers, and possibly other additives. Since these individual components react with one another, they are stored separately until the ready-to-use mass is produced. The individual components are fed to a mixing element so as to be metered in a given amount ratio, for example, by means of a press-out device, and the individual components are mixed in the mixing element to form a ready-to-use mass. This mass is then dispensed at an application site.

In order to reduce the amount of packaging material used for the multi-component masses for ecological reasons as well as for reasons of economy, e.g., tube bags of suitable foil material having a main chamber and at least one secondary chamber are used as packaging material for masses of this kind. While dispensing the individual components, the tube bag is progressively folded up and the amount of packaging to be disposed of is considerably reduced compared, for example, to hard plastic packaging. This general prior art is disadvantageous because a constant mixing ratio is not adequately ensured.

The dividing walls of the multi-chamber tube bag can be displaced or creased in an unwanted manner between the individual chambers during the press-out process so that considerable discrepancies in the mixing ratios can result. Particularly in multi-component mortars for injection-based chemical fastenings, reliable operation is ensured only if the theoretical mixing ratios of the individual components are maintained. In addition, an uneven folding of the foils can lead to malfunctions in the press-out device. When small amounts of multi-component mass must be dispensed repeatedly, the strict safety requirements, e.g., for mortars for chemical fastenings, may not be met in the packaging known from the general prior art.

A cartridge with a two-chamber bag arranged in the interior of a cartridge is known from U.S. Pat. No. 5,647,510 A. A head part comprising multiple parts is provided at the end of the cartridge on the press-out end, the free ends of the tube bag being fixed to this head part. The larger main chamber has a direct outlet into the press-out opening of the cartridge. The secondary chamber is arranged at a separate portion of the head part which has a channel portion into the press-out opening.

The known solution is disadvantageous in that the head part is complicated to produce. The head part according to U.S. Pat. No. 5,647,510 A can only be manufactured using complicated design steps particularly when connecting a multi-chamber tube bag with more than two chambers, e.g., a multi-component mass having three or more components. In addition, the amount of waste to be disposed of is substantially greater compared to a conventional multi-chamber tube bag without a head part.

SUMMARY OF THE INVENTION

It is the primary object of the invention to provide a head part for a multi-chamber tube bag which ensures an extensively constant mixing ratio, of two or more components of a chemical mass, on the one hand and can be produced simply and economically on the other hand.

According to the invention, at least one raised part is provided at the contact surface for narrowing an outlet region of at least the at least one secondary chamber of the multi-chamber tube bag when the multi-chamber tube bag bears against the contact surface.

As a result of the raised portion formed as a projection, for example, the outlet cross section is narrowed at least in some regions and the amount exiting the at least one secondary chamber is restricted or throttled during the process of dispensing the respective components. In this way, a pressure difference is built up between the one component in the main chamber and the at least one other component in the at least one secondary chamber. This pressure difference ensures that the flexible dividing wall between the main chamber and the at least one secondary chamber is loaded only by tensile forces so that they are not displaced or deformed in an unwanted manner and the reference cross-sectional surfaces or output cross-sectional surfaces of the main chamber and of the at least one secondary chamber are maintained throughout the entire dispensing process. In addition, the pressure difference can be ensured and therefore the output cross-sectional surfaces can be maintained through a suitable selection of differences in the viscosity or penetrometer values of the individual components relative to one another. As soon as the multi-chamber tube bag contacts the contact surface and it is opened and pressure is generated on the multi-chamber tube bag, e.g., by means of a press-out piston, a constant mixing ratio of the individual components relative to one another is ensured during the entire press-out process due to the design of the head part according to the invention. This ensures a constant mixing ratio of the individual components even when repeatedly dispensing small amounts of the multi-component mass.

The main chamber of the multi-chamber tube bag usually has a greater cross-sectional surface than the at least one secondary chamber. The at least one secondary chamber is advantageously arranged in an outer area of the multi-chamber tube bag. The multi-chamber tube bag advantageously has a substantially circular total cross section, and the at least one secondary chamber likewise has an approximately circular cross section.

The raised portion in the area of the entire circumference of the press-out opening is preferably arranged at the contact surface. This construction of the head part according to the invention is advantageous particularly in multi-chamber tube bags having more than two secondary chambers. In a variation of this arrangement, raised portions are formed at the contact surface which are formed correspondingly with respect to the quantity of secondary chambers in the multi-chamber tube bag and with respect to their radial extension, e.g., in a multi-chamber tube bag with a substantially circular total cross section. When the head part is arranged on the multi-chamber tube bag or when the multi-chamber tube bag is arranged at the head part, they are arranged so as to be aligned with one another in a corresponding manner.

The press-out opening is preferably arranged in an aligned manner at the contact surface with respect to the position of the outlet of the main chamber in order to enable an extensively linear flow of the component from the main chamber when the multi-chamber tube bag contacts the contact surface at the head part. When the main chamber, for example, in a multi-chamber tube bag with a substantially circular cross section, is arranged substantially centrically in the multi-chamber tube bag, the press-out opening is advantageously provided in the center of the contact surface in order to make it possible for the component to flow from the main chamber linearly to a great extent. In case of a substantially lateral arrangement of the main chamber, the press-out opening is provided at the contact surface corresponding to the position of the outlet of the main chamber. The arrangement of the outlet opening in alignment with the position of the outlet of the main chamber ensures that the predetermined amount of the one component from the main chamber is dispensed substantially directly in combination with the restricted mass flow of the at least one other component from the at least one secondary chamber.

The head part is advantageously fixed to the multi-chamber tube bag. For example, the head part is glued or welded to the multi-chamber tube bag, e.g., in situ. The head part is preferably preassembled with the multi-chamber tube bag. This makes it possible to connect the head part to the multi-chamber tube bag under controlled conditions, which improves the correct alignment of the head part to the multi-chamber tube bag or the correct alignment of the multi-chamber tube bag to the head part and the quality of the connection is improved compared to making the connection in situ. The usability of the multi-chamber tube bag is likewise improved when preassembled compared with making the connection in situ.

In another advantageous construction, the head part is a component part of a press-out device. The head part according to the invention is formed at the press-out device, e.g., at the end facing in the press-out direction of the press-out device. In a variation of this construction, the head part according to the invention is introduced into a commercially available press-out device before inserting the multi-chamber tube bag into a receiving space for the multi-chamber tube bag of the press-out device. The head part according to the invention can be reused multiple times in this construction.

In another advantageous construction, the head part is a component part of a cartridge for the multi-chamber tube bag. The cartridge has, e.g., a tubular receptacle which is provided, at the end facing in the press-out direction of the cartridge, with an opening for the multi-component mass to be dispensed. The head part according to the invention is formed at the cartridge, for example, at the end facing in the press-out direction of the cartridge.

The head part is preferably formed as the base of the cartridge for the multi-chamber tube bag. In this variation, the head part according to the invention is inserted into the receptacle of the cartridge before inserting the multi-chamber tube bag. For this purpose, the cartridge can have, at the end facing in the press-out direction of the cartridge, only one stop which limits an axial displacement of the head part in the press-out direction of the cartridge. The head part according to the invention can be reused multiple times in this construction.

In another variation, an inner tube which takes over the function of the head part according to the invention can be provided at an exchangeable mixing element which is arranged, for example, at a cartridge. The mixing element has, for example, a connection with an internal thread and the inner tube is arranged coaxial to the dispensing opening of the cartridge, so that the free end of the inner tube, as raised portion, narrows the outlet area of at least the at least one secondary chamber of the multi-chamber tube bag in the contacting state of the multi-chamber tube bag. The mixing element can also have an external thread for the connection of the mixing element to an internal thread at the dispensing opening of the cartridge, wherein the free end, as raised portion, narrows the outlet area of at least the at least one secondary chamber of the multi-chamber tube bag in the contacting state of the multi-chamber tube bag.

Further advantageous embodiment forms and combinations of features of the invention follow from the following detailed description and from the patent claims in their totality.

BRIEF DESCRIPTION OF THE DRAWINGS

The invention will be described more fully in the following with reference to several embodiment examples.

BRIEF DESCRIPTION OF THE DRAWINGS

Figure 1:
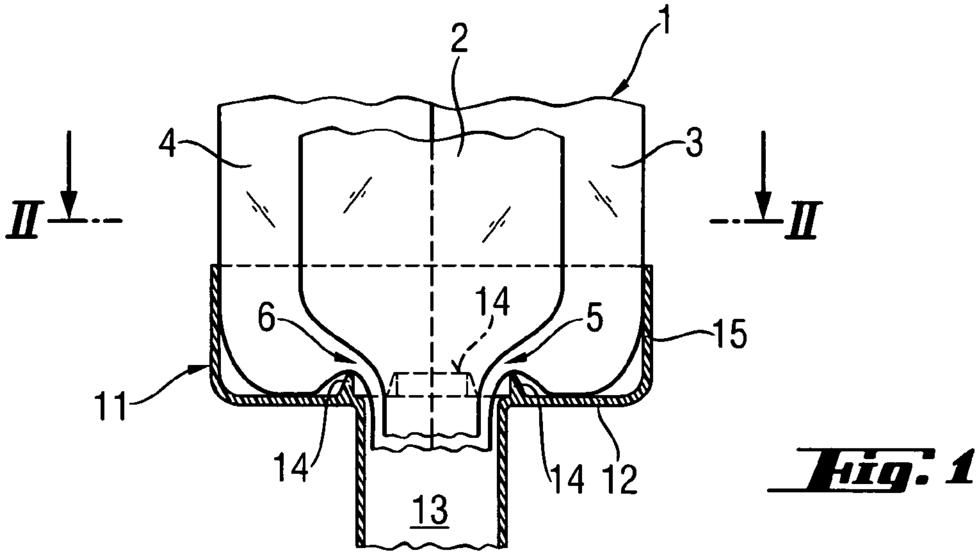
Figure 2:
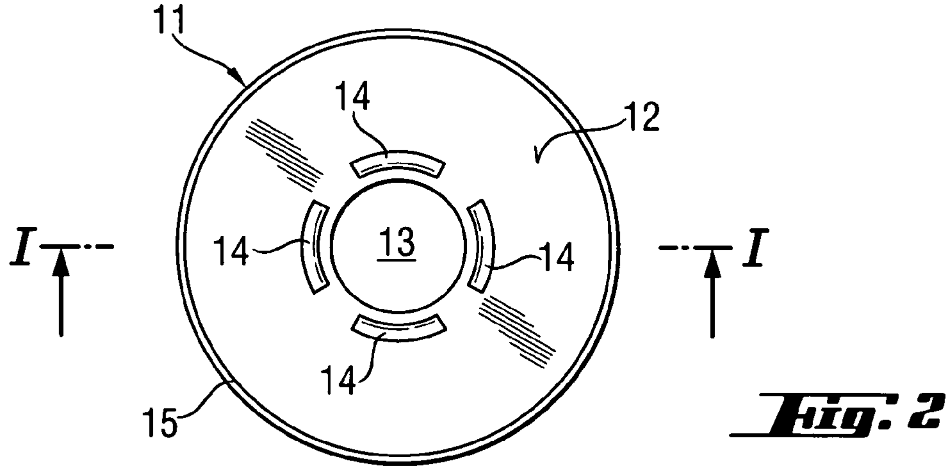
Figure 3:
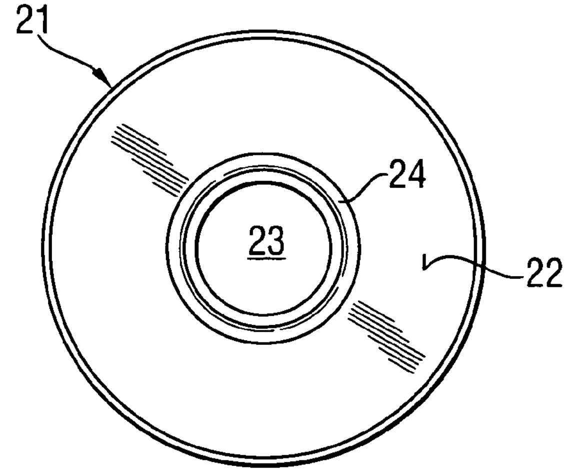
Figure 4:
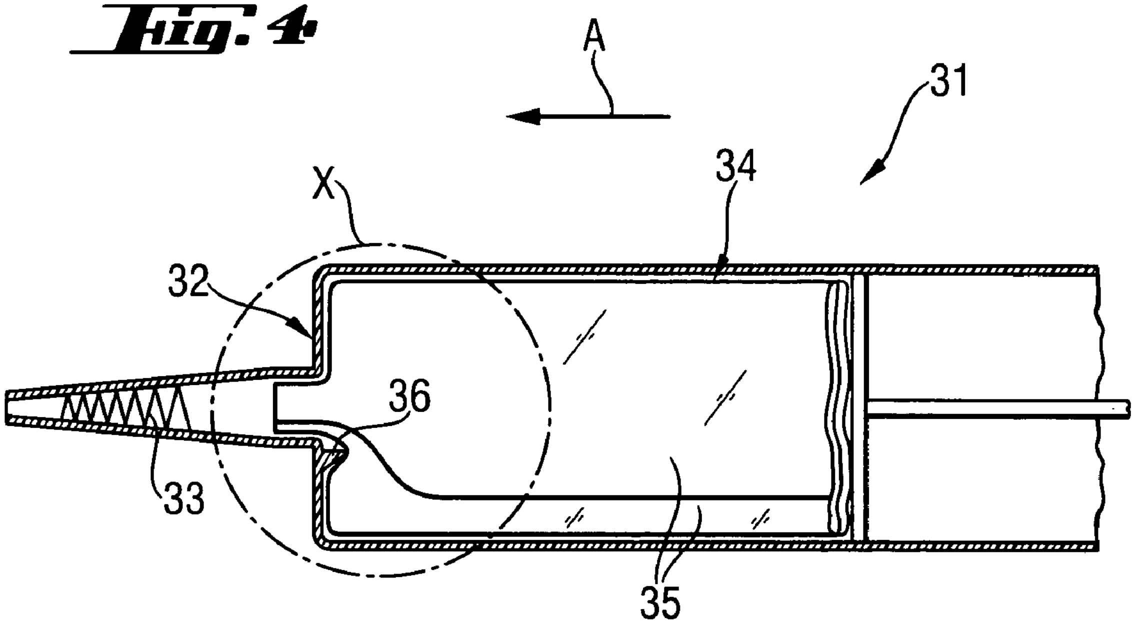
Figure 5:
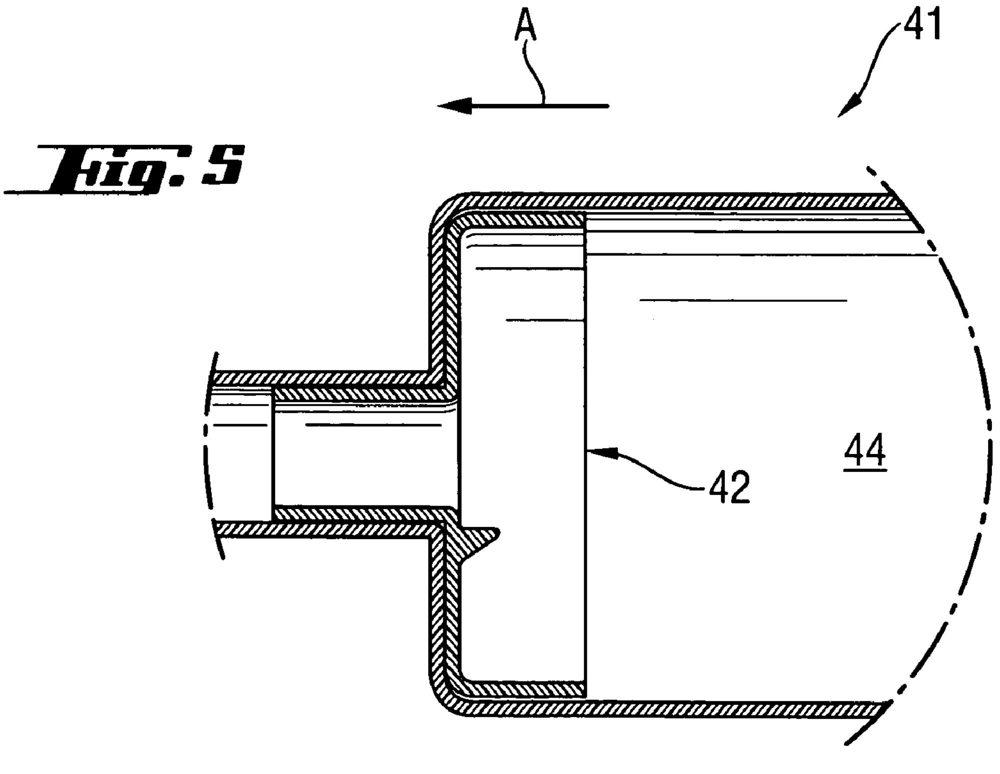
Figure 6:
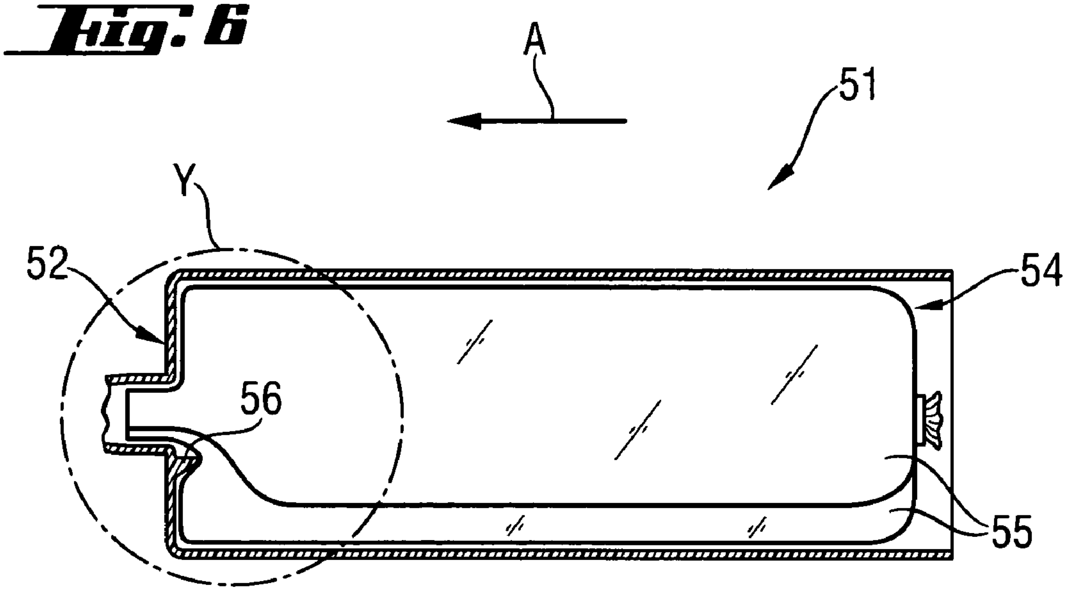
Figure 7:
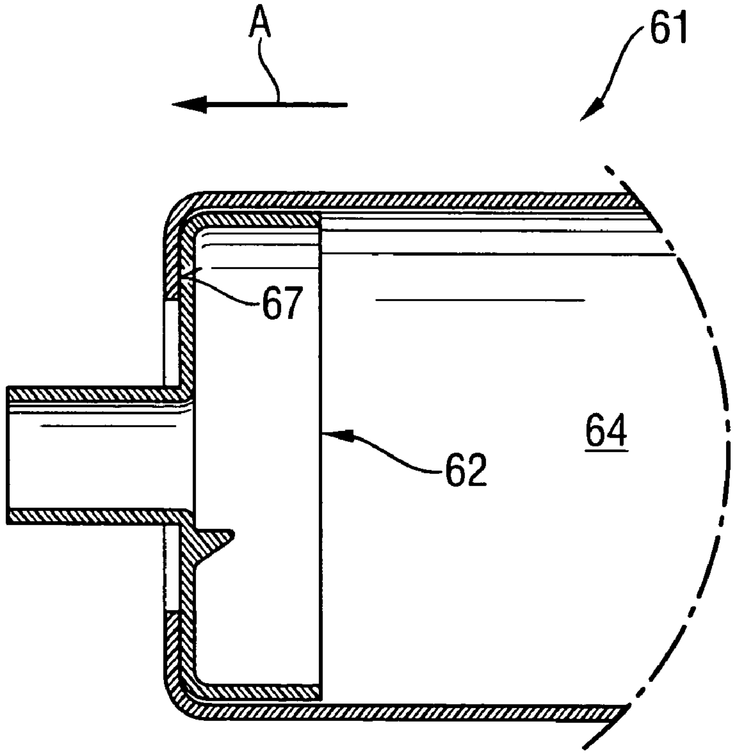

FIG. 1 shows a longitudinal section in plane I-I of FIG. 2 through the head part, according to the invention, with contacting multi-chamber tube bag;

FIG. 2 is a view of the head part shown in FIG. 1 viewed from plane II-II of FIG. 1 without the multi-chamber tube bag;

FIG. 3 is a view of a second embodiment example of the head part, according to the invention, shown in FIG. 2;

FIG. 4 shows a longitudinal section through a press-out device, shown partially, with another embodiment example of the head part according to the invention;

FIG. 5 shows an enlarged detail section through a press-out device with a variant of the head part shown in FIG. 4 in area X;

FIG. 6 shows a longitudinal section through a cartridge with another embodiment example of the head part according to the invention; and FIG. 7 shows an enlarged detail section through a cartridge with a variant of the head part shown in FIG. 6 in area Y.

Identical parts are provided with identical reference numbers in the drawings.

DETAILED DESCRIPTION OF THE INVENTION

Detailed Description of the Preferred Embodiments

FIGS. 1 and 2 show a head part 11 according to the invention which is glued to a multi-chamber tube bag 1 on the work side. The multi-chamber tube bag 1 for a three-component mass has a main chamber 2 and two secondary chambers 3 and 4 arranged at the outer circumference of the multi-chamber tube bag 1. In this embodiment example, the multi-chamber tube bag 1 has a circular cross-sectional surface in cross section.

The head part 11 has a disk-shaped contact surface 12 and a press-out opening 13. A connection for a mixer element which can be screwed on, for example, can be provided at the press-out opening 13. Further, the head part 11 has a collar 15 which at least partially encompasses the end area of the multi-chamber tube bag 1. Four raised parts 14 which are constructed as projections and which are oriented in the direction of the multi-chamber tube bag 1 are formed at the contact surface 12. The raised parts 14 narrow the outlet area 5 of the secondary chamber 3 and the outlet area 6 of the secondary chamber 4 in the state in which the multi-chamber tube bag 1 contacts the head part 11.

When pressure is applied and after the multi-chamber tube bag 1 is opened, the components in the main chamber 2 can exit substantially linearly due to the centric arrangement of the press-out opening 13 at the contact surface 12. In contrast, the components from the secondary chambers 3 and 4 are guided together in the press-out opening 13 in a throttled manner due to the narrowing in the outlet areas 5 and 6 of the secondary chambers 3 and 4, respectively, with the components from the main chamber 2 and are jointly supplied to a mixing element for producing the ready-to-use multi-component mass. The pressure difference generated in the chambers 2, 3 and 4 of the multi-chamber tube bag 1 due to the throttling in the outlet areas 5 and 6 ensures the alignment of the dividing walls in the multi-chamber tube bag 1 during the entire dispensing process so as to ensure a constant mixing ratio of the components relative to one another.

FIG. 3 shows a variation of the head part 11 according to FIG. 2. The head part 21 has, at the contact surface 22, a raised portion 24 which is constructed as a projection, and extends annularly around the press-out opening 23 and is constructed along the entire circumference so as to be offset radially outward in the region of the press-out opening 23.

FIG. 4 shows a press-out device 31 with a receiving space 34 for a two-chamber tube bag 35 which has, at its end facing in the press-out direction A, a head part 32 according to the invention which is connected integral with the press-out device 31. A mixing element 33 is arranged at the head part 32. The head part 32 has a raised part 36 at the side facing the receiving space 34.

FIG. 5 shows a variant of the press-out device 31 according to FIG. 4 in which the head part 42 is inserted as a separate part into the receiving space 44 of the press-out device 41 before the insertion of the multi-chamber tube bag.

FIG. 6 shows a cartridge 51 with a receiving space 54 for a two-chamber tube bag 55 which has, at its end facing in the press-out direction A, a head part 52 according to the invention that is connected integral with the cartridge 51. The head part 52 has a raised portion 56 at the side facing into the receiving space 54.

FIG. 7 shows a variant of the cartridge 51 according to FIG. 6 in which the head part 62 is inserted as a separate part in the receiving space 64 of the cartridge 61 before inserting the multi-chamber tube bag. At the end facing in the press-out direction A, the cartridge 61 is provided with a stop 67 which limits the axial displacement of the head part 62 in the press-out direction A.

What is claimed is:

1. Head part for a multi-chamber tube bag (1; 35; 55) containing a multi-component mass which can be pressed out of said bag, said bag having a main chamber (2) arranged for holding a first component and at least one secondary chamber (3,4) at least partially laterally enclosing the main chamber for another component to be mixed with the first component, the head part (11; 32; 42, 52; 62) comprising:

a substantially flat contact surface (12;22) facing a discharge end surface of said multi-chamber tube bag, said contact surface surrounds a tubular press-out opening (13; 23) extending outwardly away from said tube bag (1; 35; 55) and aligned with the main chamber, said contact surface (12; 22) having at least one raised part (14; 24; 36; 56) arranged in the direction of the discharge end surface of the multi-chamber tube bag (1; 35; 55), with the at least one raised part (14; 24; 36; 56) in contact with the contact surface of the head part simultaneous with the at least one raised part (14; 24; 36; 56) of the contact surface (12; 22) being aligned to the multi-chamber tube bag (1; 35; 55), and with the at least one raised part (14; 24; 36; 56) extending therefrom opposite into contact with said secondary chamber to said press-out opening for narrowing an outlet opening of at least one said secondary chamber (3;4) into said press-out opening (13;23) and for throttling the flow from the secondary chamber;

wherein said head part (52, 62) is a component part of a cartridge for laterally enclosing said multi-chamber tube bag (55); and wherein said head part (62) is formed as a base of said cartridge for the said multi-chamber tube bag (55).

2. A multi-chamber tube bag (1; 35; 55) containing a multi-component mass which can be pressed out of the bag, multi-chamber tube bag (1; 35; 55) comprising:

a main chamber (2) arranged for holding a first component;

at least one secondary chamber (3,4) at least partially laterally enclosing the main chamber (2) for another component to be mixed with the first component; and a head part (11; 32; 42, 52; 62) having a substantially flat contact surface (12;22) facing a discharge end surface of the multi-chamber tube bag, the contact surface surrounds a tubular press-out opening (13; 23) extending outwardly away from the tube bag (1; 35; 55) and aligned with the main chamber, the contact surface (12; 22) having at least one raised part (14; 24; 36; 56) arranged in the direction of the discharge end surface of the multi-chamber tube bag (1; 35; 55), with the at least one raised part (14; 24; 36; 56) in contact with the contact surface of the head part simultaneous with the at least one raised part (14; 24; 36; 56) of the contact surface (12; 22) being aligned to the multi-chamber tube bag (1; 35; 55), and with the at least one raised part (14; 24; 36; 56) extending therefrom opposite into contact with the secondary chamber to the press-out opening for narrowing an outlet opening of at least one the secondary chamber (3;4) into the press-out opening (13;23) and for throttling the flow from the secondary chamber;

wherein the head part (52, 62) is a component part of a cartridge for laterally enclosing the multi-chamber tube bag (55); and wherein the head part (62) is formed as a base of the cartridge for the multi-chamber tube bag (55).

* * * * *